United States Patent [19]

Sipos

[11] 4,091,090
[45] May 23, 1978

[54] POTENTIATED ANESTHETICS

[75] Inventor: Tibor Sipos, Jackson, N.J.

[73] Assignee: Johnson & Johnson, New Brunswick, N.J.

[21] Appl. No.: 748,868

[22] Filed: Dec. 10, 1976

Related U.S. Application Data

[60] Division of Ser. No. 595,986, Jul. 14, 1978, Pat. No. 4,006,218, which is a continuation of Ser. No. 486,287, Jul. 8, 1974, abandoned, which is a continuation-in-part of Ser. No. 285,682, Sep. 1, 1972, abandoned.

[51] Int. Cl.$^2$ ............... A61K 31/445; A61K 31/045; A61K 31/165; A61L 9/04
[52] U.S. Cl. .................................. 424/45; 424/267; 424/310; 424/324; 424/343
[58] Field of Search ............... 424/343, 324, 310, 267, 424/45

[56] References Cited

U.S. PATENT DOCUMENTS 3,891,757  6/1975  Higuchi ........................ 424/310

Primary Examiner—Sam Rosen

[57] ABSTRACT

Topical anesthetic compositions are provided wherein there is obtained an enhancement of the activity of the topical anesthetic agent by combining the anesthetic agent with an effective amount of a penetrant accelerator selected from the group consisting of the cyclohexyl substituted alkanols of the structure

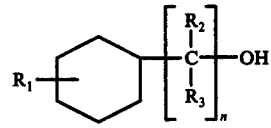

wherein $R_1$ is $C_1$ to $C_4$ alkyl, halogen or hydrogen; $R_2$ and $R_3$ are independently selected from hydrogen, $C_1$ to $C_3$ alkyl, and cyclopropyl; and $n$ is 1 to 4, provided that only one of $R_2$ and $R_3$ may be propyl or cyclopropyl.

The topical anesthetic compositions of the invention are applied to the skin of an animal in order to induce anesthesia topically in the animal.

25 Claims, No Drawings

POTENTIATED ANESTHETICS

CROSS-REFERENCE TO RELATED APPLICATIONS

This application is a division of application Ser. No. 595,986, filed July 14, 1975, now U.S. Pat. No. 4,006,218, issued Feb. 1, 1977, which application is in turn a continuation of application Ser. No. 486,287, filed July 8, 1974, now abandoned, which application is in turn a continuation-in-part of application Ser. No. 285,682, filed Sept. 1, 1972, now abandoned.

BACKGROUND OF THE INVENTION

In one aspect, this invention relates to antimicrobial compositions. More particularly, it relates to the discovery that a broad group of known antimicrobial agents have increased activity, either in terms of spectrum, killing power, or both, when used in combination with the potentiating agents of this invention.

Ordinarily, the activity or killing power of known antimicrobial agents are inhibited in the presence of blood, wound exudates and other proteinaceous matter including serum proteins, together with saliva, sebaceous secretions, nasal and other mucous secretions.

Although it has been realized for some time that antibacterial agents lose their efficacy in the presence of blood, bodily secretions such as milk serum and wound exudates, the cause of this loss of efficacy or inactivation is not as yet fully understood. It has been postulated, however, that the lipophilic character of the antimicrobial agent is responsible for both protein binding and antimicrobial activity. In the presence of such extraneous proteinaceous matter as blood, the antimicrobial agent preferentially binds to the serum proteins or other proteinaceous matter rather than to the bacterial cells. Under conditions where this undesired preferential binding can occur, the antimicrobial agent is either ineffective or its efficacy is so reduced that greatly increased dosage levels are required. The extent of this loss in activity can approach 90 percent or more. For example, the antimicrobial activity of quaternary ammonium compounds can be so suppressed in the presence of proteinaceous body fluids that activity losses in excess of 96 percent have been recorded.

While the lack of precise knowledge and understanding of the inactivation mechanism has hampered the development of topical antimicrobial preparations which are effective in the presence of the inactivating materials above referred to, it has long been a desired and sought for goal to develop antimicrobial compositions that could overcome this inactivation.

Therefore, an important feature of the present invention is to provide compositions which include known antibacterial, antiviral or antifungal agents together with a potentiator for such agents so as to overcome the deactivating effect of proteinaceous substances and to significantly increase the killing efficacy or to extend the antimicrobial spectrum of the antimicrobial agent, or to have both enhancing effects.

Enhancement of drug absorption through the intact skin has been pursued by many investigators in recent times. Most of these studies showed that the stratum corneum of the skin, the uppermost or horny layer, acts as a protective barrier against the exterior environment. The stratum corneum consists of dead cells that are extensively keratinized and dehydrated. Due to the nature of the highly crosslinked and insoluble keratin, the barrier property of this layer changes little upon exposure to various environmental conditions.

Because of the impermeable nature of the stratum corneum, it has been a long desired goal to temporarily modify the barrier property of this layer in order to enhance the penetration of topically applied drugs. Especially in dermatological conditions, topical application of medicaments is preferred over systemic administration, because the topically applied drug directly attacks the affected target cells. Furthermore, topical treatment eliminates systemic side effects that are frequently associated with long term oral therapy.

Previous studies have shown that dimethylsulfoxide (DMSO) can enhance the absorption of topically applied drugs through the stratum corneum. Similarly, dimethyl formamide (DMFA) and N,N-dimethyl-acetamide (DMA) and their derivatives are claimed to do the same. Some of these combinations are described in U.S. Pat. Nos. 3,551,554 and 3,472,931.

Other recent studies on the physico-chemical properties of the stratum corneum and the absorption of topically applied drugs therethrough include: Scheuplein, R. J., J. Invest. Dermatol. 45, 334 (1966); Blank, I. H., J. Invest. Dermatol, 43, 415 (1964); Hadgraft, J. W. and Somers, G. F., J. Parm. Pharmacol. 8, 625 (1956); and Grasso, P. and Lansdown, A. B. G., J. Soc. Cosmet. Chem. 23, 481-521 (1972).

Thus, in accordance with another feature of the present invention, there are provided topical compositions comprising a known medicament, exemplified by the anesthetics, and a potentiator, whereby the penetration of topically applied anesthetic or other agents through the stratum corneum are substantially enhanced. As an example, enhanced penetration of the anesthetic agent by the action of the potentiator or accelerator results in a quicker onset and deeper anesthesia at the treated site, than that which is obtained without the accelerator. Furthermore, anesthesia at the site of application lasts up to several hours. Conventional preparations elicit only surface anesthesia and onset times sometimes extend to hours. Most conventional preparations, moreover, have been reported to be ineffective on intact skin [Adriani, J. and Dalili, H. Anesthesia and Analgesia, Current Researches, Vol. 50, No. 5 (Sept.-Oct. 1971)].

SUMMARY OF THE INVENTION

It has now been discovered that the foregoing and other advantages which will become apparent upon further reading are achieved, in one embodiment of the invention, by providing an antimicrobial composition which includes, together with an antimicrobial agent, a potentiator therefor as defined herein. The antimicrobial agent can be selected from the group consisting of quaternary ammonium compounds, bisdiquanides, antifungal agents, phenols, hydroxydiphenyls, carbanilides, salicylanilides, organometallic antiseptics, antibiotics, iodine and organic iodine derivatives and iodophores derived from nonionic wetting agents and from polyvinylpyrrolidone, and is used in accordance with the present invention in combination with a potentiator of the type hereinafter described.

It has also been discovered, in accordance with another embodiment of the present invention, that enhanced penetration through the skin of known medicaments and increased topical activity thereof is provided by a composition comprising a known medicament in combination with a selected penetration accelerating potentiator therefor. The medicament may be selected from the group consisting of anesthetics, antiinflammatory agents, antimicrobial agents including antibacterial and antiviral agents, cell regulatory agents and the like. The potentiators for this aspect of the invention; as hereinafter defined, include many of the compounds which are useful as potentiators in the antimicrobial compositions of the present invention.

As used herein, the term "potentiator" is meant to indicate on the one hand, that the compound enhances the activity of an antimicrobial agent over what it ordinarily would be if otherwise used alone. It also will be seen later that a number of combinations of antimicrobial agents and potentiators of the invention can be considered to have a synergistic effect in that the spectrum of the antimicrobial composition is extended to organisms which are not susceptible to either the antimicrobial agent or the potentiator when each is individually employed at an equivalent concentration. For example, griseofulvin when combined with the potentiator 2,3-dimethyl-2-hexanol is effective against the otherwise resistant Candida albicans.

Enhanced activity, or potentiation, is also exhibited by the various potentiator-antimicrobial combinations of the present invention not only when the spectrum of activity of the combinations of this invention is broader than when either component of the combinations is used alone, but also in substantially greater activity of the combination against a given organism than could be accounted for by a simple additive effect. Potentiation of the topical compositions of the present invention may be exhibited by either or both of enhanced penetration through skin or a like biological barrier and greater activity than could be expected from any additive effects of the active compound and the potentiator.

DESCRIPTION OF THE PREFERRED EMBODIMENTS

Antimicrobial Compositions

The antimicrobial compositions of the invention comprise an antimicrobial agent and a potentiator therefor. In use, the combination of antimicrobial agent and potentiator is preferably dissolved, suspended to dispersed in a suitable carrier. Although generally not as desirable as employing a separate carrier, it has been found suitable to employ the same chemical compound as both the potentiator and the carrier, thus eliminating the need for a separate carrier or vehicle.

Antimicrobial Agents

Examples of antimicrobial agents which may be employed in the potentiated antimicrobial compositions of this invention include the antibiotics such as tetracycline, oxytetracycline, chlorotetracycline, neomycin, erythromycin and its derivatives, bacitracin, streptomycin, rifampicin and its derivatives, such as N-demethyl-rifampicin, kanamycin and chloromycetin; the anti-fungal agents such as griseofulvin, mycostatin, miconazole, and its derivatives as described in U.S. Pat. No. 3,717,655; bisdiguanides such as chlorhexidine; quaternary ammonium compounds such as domiphen bromide, domiphen chloride, domiphen fluoride, benzalkonium chloride, cetyl pyridinium chloride, dequalinium chloride, the cis isomer of 1-(3-chloroallyl)-3,5,7-triaza-1-azoniaadamantane chloride (available commercially from the Dow Chemical Company under the trademark Dowicil 200) and its analogues as described in U.S. Pat. No. 3,228,829, cetyl trimethyl ammonium bromide as well as benzethonium chloride and methylbenzethonium chloride such as described in U.S. Pat. Nos. 2,170,111, 2,115,250 and 2,229,024; the carbanilides and salicylanilides such as 3,4,4'-trichlorocarbanilide, and 3,4'5-tribromosalicylanilide; the hydroxydiphenyls such as dichlorophene, tetrachlorophene, hexachlorophene, and 2,4,4'-trichloro-2'-hydroxydiphenylether; and organometallic and halogen antiseptics such as zinc pyrithione, silver sulfadiazine, silver uracil, iodine, and the iodophores derived from non-ionic surface active agents such as are described in U.S. Pat. Nos. 2,710,277 and 2,977,315 and from polyvinylpyrrolidone such as described in U.S. Pat. Nos. 2,706,701, 2,826,532 and 2,900,305.

Potentiators

The potentiators which can be suitably employed in the antimicrobial compositions of this invention include members selected from the group consisting of:

I. Primary, secondary and tertiary straight or branched chain monohydric aliphatic alcohols, wherein the straight chain alcohols have from about 5 to about 10 carbon atoms and the branched chain alcohols have up to about 17 carbon atoms, their longest chain of carbon to carbon bonds having from about 5 to about 10 carbon atoms;

II. A cyclohexyl substituted alkanol of the structure

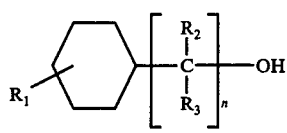

wherein $R_1$ is $C_1$ to $C_4$ alkyl, halogen or hydrogen; $R_2$ and $R_3$ are independently selected from hydrogen, $C_1$ to $C_3$ alkyl, and cyclopropyl; and $n$ is 1 to 4, provided that only one of said $R_2$ and $R_3$ of a

moiety may be propyl or cyclopropyl;

III. Phenyl alkanols of the structure

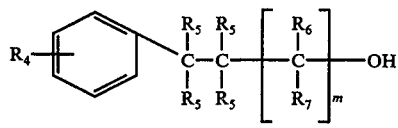

wherein $m$ is 0 or 1; $R_4$ is hydrogen, halogen, $C_1$ to $C_4$ alkyl, or cyclopropyl; $R_5$, $R_6$ and $R_7$ are independently selected from hydrogen, $C_1$ to $C_3$ alkyl and cyclopropyl, provided, however that only one of $R_5$, $R_6$ and $R_7$ is a propyl or cyclopropyl group, and, when $m$ is 0, at least one $R_5$ is other than hydrogen; and the total of the carbon atoms in the structure

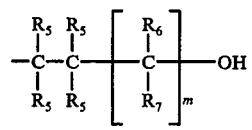

is from 3 to 9 carbon atoms; and

IV. Phenol derivatives of the structure

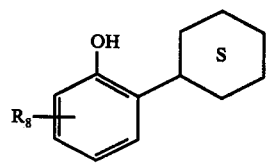

where $R_8$ is hydrogen, $C_1$ to $C_3$ alkyl, $C_1$ to $C_3$ alkoxy, hydroxy, halogen, amino, or mono or di $C_1$ to $C_3$ alkyl amino, provided that the total number of carbon atoms in the alkyl groups substituted on the amino does not exceed 5 carbon atoms. Preferably, when $R_8$ is halogen, di-$C_1$ to $C_3$ alkylamino, or $C_1$ to $C_3$ alkoxy, then $R_8$ is para to the phenolic hydroxyl group.

Examples of the preferred aliphatic alcohol potentiators from Group I include: n-hexanol; n-heptanol; n-octanol; n-nonanol; n-decanol; 2,3-dimethyl-2-hexanol; 2,5-dimethyl-2-hexanol; 2-methyl-3-hexanol; 2-heptanol; 3-heptanol; 4-heptanol and 2-ethyl-1-hexanol.

Examples of the preferred potentiators from Group II include: cyclohexylmethanol; 1-cyclohexylethanol; 2-cyclohexylethanol; 1-cyclohexyl-1-propanol; (cyclohexyl)-dimethyl-carbinol; (4-isopropylcyclohexyl)-dimethylcarbinol; 3-cyclohexyl-1-propanol; 2-cyclohexyl-1-propanol; 1-cyclohexyl-2-propanol; 2-cyclohexyl-1,1-dimethylethanol; 2-cyclohexyl-2-methylpropanol; 2-cyclohexyl-1-methylpropanol; 2-cyclohexyl-1,2-dimethylpropanol; 2-cyclohexyl-1,1-dimethylpropanol; 3-cyclohexyl-2-methylpropanol; 3-cyclohexyl-1-methylpropanol; 3-cyclohexylbutanol; 3-cyclohexyl-2-methylbutanol; and 3-cyclohexyl-1,2-dimethylbutanol.

Preferred examples from Group III include: 3-phenyl-1-propanol; benzyl-t-butanol; 1-(p-chlorophenyl)-2-methyl-2-propanol, 1-phenyl-2-methyl-2-propanol; 1-phenyl-3-butanol; 2-methyl-3-phenyl-propanol; 2,2-dimethyl-3-phenyl-propanol; 3(-p-chlorophenyl) propanol; 4(-p-chlorophenyl)-2-butanol; 2,2-dimethyl-3(p-chlorophenyl)-propanol, 2-methyl-3(p-chlorophenyl)-propanol; 1-phenyl-2-propanol; and 1-(p-chlorophenyl)-2-propanol.

Preferred examples from Group IV include: 2-cyclohexylphenol; 4-cyclohexylresorcinol; 2-chloro-6-cyclohexylphenol; 4-amino-2-cyclohexylphenol hydrochloride; o-cyclohexyl-p-methoxyphenol; o-cyclohexyl-p-cresol; o-(4-methylcyclohexyl)-p-cresel; and 4-chloro-2-cyclohexylphenol.

ILLUSTRATIVE ANTIMICROBIAL COMPOSITIONS

The antimicrobial compositions of this invention include at least one antimicrobial agent and at least one of the potentiators selected from Groups I, II, III and IV. In general, the composition comprises at least 0.1 percent of the potentiator and at least 0.001 percent of the antimicrobial agent. However amounts of as little as 0.05 percent potentiator have been found to be effective when the potentiator is selected from compounds of Group IV. The balance of the composition, if any, is supplied by a suitable carrier as is hereinafter described. Generally, the antimicrobial agent is employed in a quantity less than that of the potentiator. It is entirely suitable that up to 99.999% of the composition be potentiator, thus obviating the need for using as additional component as a carrier. However, if desired, a carrier, preferably ethanol, can be employed. The more desirable compositions comprise from 0.1 to 90.0 percent potentiator and 0.001 to about 10.0 percent antimicrobial agent, and preferably from 0.1 to 10.0 percent potentiator and from 0.001 to 0.5 percent antimicrobial agent, depending on the particular materials used, with the balance of the composition comprising a suitable carrier, or combination of carriers. Examples of such compositions are ethanol solutions of: 0.05% miconazole and 0.50% 1-cyclohexylethanol; 0.05% neomycin sulfate and 0.60% 2-cyclohexylethanol; 0.50% tetracycline and 0.75% n-hexanol; 0.05% tetracycline and 0.50% 1-cyclohexylethanol; 0.05% neomycin sulfate and 0.75% 2,3-dimethyl-2-hexanol; 0.05% neomycin sulfate and 0.75% 1-cyclohexylethanol; 0.75% iodine and 0.40% 2-cyclohexylethanol; and 0.05% 3,3',4,5'-tetrachlorosalicylanilide and 0.50% 1-cyclohexylethanol.

Examples of the antimicrobial compositions of this invention where there is a synergistic effect provided by the combination of the antimicrobial agent and the potentiator include ethanol solutions of: 0.05% 3,3',4,5-tetrachlorosalicylanilide and 0.50% n-hexanol; 0.025% dequalinium chloride and 0.50% 1-(p-chlorophenyl)-2-methyl-2-propanol; 0.025% domiphen bromide and 1.0% n-pentanol; 0.025% domiphen bromide and 0.75% 2-heptanol; 0.025% domiphen bromide and 0.50% 2,3-dimethyl-2-hexanol; 0.025% domiphen bromide and 0.75% 2,3-dimethyl-2-hexanol; 0.0125% domiphen bromide and 0.6% hexanol; 0.05% hibitane and 0.10% 2-cyclohexylphenol; 0.05% griseofulvin and 0.75% hexanol; 0.05% griseofulvin and 0.5% 2,3-dimethyl-2-hexanol; 0.05% griseofulvin and 0.75% 2,3-dimethyl-2-hexanol; 0.05% griseofulvin and 0.5% 1-cyclohexylethanol; 0.05% griseofulvin and 0.75% 1-cyclohexylethanol; 0.05% tetracycline and 0.5% 1-(p-chlorophenyl)-2-methyl-2-propanol; 0.1% zinc pyrithione and 0.5% 1-cyclohexylethanol; 0.1% zinc pyrithione and 0.75% 2,3-dimethyl-2-hexanol; 1.0% zinc pyrithione and 0.5% 1-(p-chlorophenyl)-2-methyl-2-propanol; and 0.5% zinc pyrithione and 0.6% 2-cyclohexylethanol.

In use, the antimicrobial agent and the potentiator are conveniently dissolved or dispersed in an inert fluid medium which serves as a carrier. The term inert means that the carrier does not have a deleterious effect on the antimicrobial agent upon storage, nor substantially diminish its activity, nor adversely react with any other component of the composition of this invention. Suitable carriers include water, lower alkanols such as ethanol, the known pharmaceutical vehicles such as conventionally employed for topical applications such, for example, as ointments, creams, lotions, aerosols, suspensions and solutions. The preferred carriers are ethanol and water.

Topical Compositions

The topical compositions of the present invention exhibiting enhanced penetration through the intact skin or enhanced topical activity comprise, in admixture, a medicament, for example, an anesthetic compound, such as lidocaine, benzocaine, tetracain, carbocaine, rodocaine, etc., with a potentiator. This may be employed in any of the known forms for applying medicaments topically, including solutions, creams, gels and the like. Preferably both the known medicament and the potentiator are dissolved, suspended or dispersed in a suitable carrier. As in the case of the antimicrobial compositions of the present invention, the potentiator may also serve as the carrier, although, generally, a separate pharmaceutically acceptable carrier is preferred, and an aqueous carrier is particularly preferred.

Potentiators

For the topical compositions of the present invention, the potentiator is selected from the group consisting of:

I. Primary, secondary and tertiary straight or branched chain monohydric aliphatic alcohols wherein the straight chain alcohols have from about 5 to about 10 carbon atoms and the branched chain alcohols have up to about 17 carbon atoms, their longest chain of carbon to carbon bonds having from about 5 to about 10 carbon atoms;

II. A cyclohexyl substituted alkanol of the structure

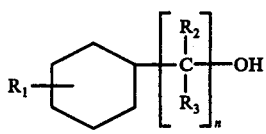

wherein $R_1$ is $C_1$ to $C_4$ alkyl, halogen or hydrogen; $R_2$ and $R_3$ are independently selected from hydrogen, $C_1$ to $C_3$ alkyl, and cyclopropyl; and $n$ is 1 to 4, provided that only one of said $R_2$ and $R_3$ of a

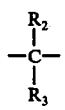

moiety may be propyl or cyclopropyl; and

III. Phenyl alkanols of the structure

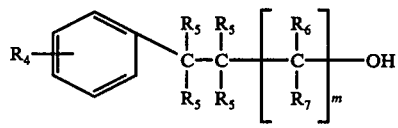

wherein $m$ is 0 or 1; $R_4$ is hydrogen, halogen, $C_1$ to $C_4$ alkyl, or cyclopropyl; $R_5$, $R_6$ and $R_7$ are independently selected from hydrogen, $C_1$ to $C_3$ alkyl and cyclopropyl, provided, however, that only one of $R_5$, $R_6$ and $R_7$ is a propyl or cyclopropyl group, and when $m$ is 0, at least one $R_5$ is other than hydrogen; and the total of the carbon atoms in the structure

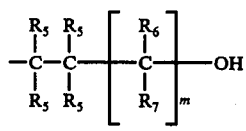

is from 3 to 9 carbon atoms.

Examples of the preferred aliphatic alcohol potentiators from Group I include: n-pentanol; n-hexanol; n-heptanol; n-octanol; n-nonanol; n-decanol; 2,3-dimethyl-2-hexanol; 2,5-dimethyl-2-hexanol; 2-methyl-3-hexanol; 2-heptanol; 3-heptanol; 4-heptanol and 2-ethyl-1-hexanol.

Examples of the preferred potentiators from Group II include: cyclohexylmethanol; 1-cyclohexylethanol; 2-cyclohexylethanol; 1-cyclohexyl-1-propanol; (cyclohexyl)-dimethyl-carbinol; (4-isopropylcyclohexyl)-dimethylcarbinol; 3-cyclohexyl-1-propanol; 2-cyclohexyl-1-propanol; 1-cyclohexyl-2-propanol; 2-cyclohexyl-1,1-dimethylethanol; 2-cyclohexyl-2-methylpropanol; 2-cyclohexyl-1-methylpropanol; 2-cyclohexyl-1,2-dimethylpropanol; 2-cyclohexyl-1,1-dimethylpropanol; 3-cyclohexyl-2-methylpropanol; 3-cyclohexyl-1-methylpropanol; 3-cyclohexylbutanol; 3-cyclohexyl-2-methylbutanol; and 3-cyclohexyl-1,2-dimethylbutanol.

Preferred examples from Group III include: 3-phenyl-1-propanol; benzyl-t-butanol; 1-phenyl-2-methyl-2-propanol; 1-phenyl-3-butanol; 2-methyl-3-phenylpropanol; 2,2-dimethyl-3-phenylpropanol; and 1-phenyl-2-propanol.

It will be seen that many of the foregoing potentiators for use in the topical compositions of the present invention are also useful as potentiators for the antimicrobial compositions. Indeed, as will become more apparent from the following discussion, many of the antimicrobial compositions disclosed above are also useful topically, and fall within the scope of the topical compositions of the present invention. Thus, the main difference between the two sets of potentiators is that the potentiators of Group IV for the antimicrobial compositions have not been found to be particularly effective for enhancing penetration of medicaments through intact skin.

Topical medicaments

The medicaments of which may be used in the topical compositions of the invention include antimicrobial agents, such as the antibiotics, for example, tetracycline, oxytetracycline, chlorotetracycline, neomycin, erythromycin and its derivatives, cycloserine, bacitracin, streptomycin, rifampicin and its derivatives, such as N-demethylrifampicin, kanamycin and chloromycetin; the antifungal agents such as griseofulvin, mycostatin, miconazole, and its derivatives as described in U.S. Pat. No. 3,717,655; quaternary ammonium compounds such as domiphen bromide, domiphen chloride, domiphen fluoride, benzalkonium chloride, cetyl pyridinium chloride, dequalinium chloride; and organometallic and halogen antiseptics such as zinc pyrithione, sodium pyrithione, silver sulfadiazine, silver uracil, iodine, and the iodophores derived from nonionic surface active agents such as are described in U.S. Pat. Nos. 2,710,277 and 2,977,315 and from polyvinylpyrrolidone such as described in U.S. Pat. Nos. 2,706,701, 2,826,532 and 2,900,305. Other medicaments whose penetriation through the skin and topical activity are enhanced, and may thus be used in the topical compositions of the present invention include antiviral and cell regulatory agents such as 5-iodo-2'-deoxyuridine, 5-iodo-2'-deoxyuridine triphosphate, 5-bromouraeyl, 5-fluorouracyl, cyclic adenosine monophosphate (c-AMP), cyclic adenosine monophosphate dibutyrate (c-AMP-dibutyrate), cyclic adenosine monophosphate succinate, cyclic guanosine monophosphate (c-GMP), methotrexate,6-azauridine triacetate (azaribin), epinephrine, phenephrine, L-dihydroxyphenyl alanine (1-DOPA) and dopamine.

A particularly preferred application of the topical compositions of the present invention is as topical anesthetic compositions, and much of the remainder of the discussion of the topical compositions of the present invention will be directed to such compositions for illustrative purposes. Suitable anesthetic agents for use in the topical anesthetic compositions of the present invention include lidocaine, benzocaine, tetracain, carbocain, radocain and the like.

Illustrative Topical Compositions

The topical compositions of this invention include at least one medicament, e.g. an anesthetic agent, and one or more of the potentiators selected from Groups I, II and III above. The anesthetic compositions comprise at least 0.5% by weight of the anesthetic agent, and a potentiating amount of the potentiator or penetrant accelerator, sufficient to enhance the skin penetration of the anesthetic agent, with the rest of the composition, if any, comprising one or more of ethanol, water and other conventional vehicles. Generally, beyond a concentration of about 15 to 18% by weight of potentiator no further enhancement of the penetration or activity of the anesthetic is observed. Thus, while more potentiator could be used, for example as the vehicle, there is no particular advantage in using a concentration of potentiator in excess of about 15% by weight. A preferred range for the concentration of potentiator is from about 1% to about 12% by weight of the composition. A preferred range for the concentration of anesthetic is from about 1% to about 10% by weight, although as much as 12% by weight or more may be employed.

Suitable vehicles include water, lower alcohols such as ethanol and isopropanol, propylene glycol, and other conventionally employed pharmaceutical vehicles for topical application such as ointments, creams, lotions, aerosols, suspensions and solutions. Preferably the topical composition contains from about 10% to about 50% by weight of water, more preferably, from about 20% to about 40% water.

Examples of such compositions are ethanol solutions of 4% lidocaine and 12% 2-cyclohexylethanol; 4% iodocaine and 6% 2-cyclohexyl-1,1-dimethylethanol; 4% carbocaine and 6% 2-cyclohexyl-2-methylpropanol; 3% tetracaine and 8% 2-cyclohexyl-1-methylpropanol; 6% benzocaine and 6% 1-cyclohexyl-1-propanol; 4% rodocaine and 12% n-hexanol; 4% lidocaine and 8% benzyl-t-butanol; 2% tetracaine and 8% 3-phenyl-1-propanol; and the like.

Currently available topically used anesthetic preparations are generally ineffective or only partially effective when applied onto intact skin. One preparation that has been shown to be effective to cause surface anesthesia contains 20% benzocaine. This high concentration of benzocaine is believed to be undesirable and dangerous because of possible toxic side effects.

A significant improvement in the speed of action and in the duration of efficacy of the currently used anesthetics can be achieved when they are combined with a penetrant accelerator in accordance with the present invention. Some of the accelerators themselves possess anesthetic activity and it is conceivable that their combination with the conventional anesthetics (lidocaine, benzocaine, carbocaine, etc.) results in the potentiation of their anesthetic activity. In addition, it is postulated that the potentiators themselves after membrane permeability and enhance the penetration of the anesthetics into the receptor sites even through the intact skin and cell membranes. Because of this unique ability of the accelerators to alter the permeability barrier of the skin and also of the cell membranes, low concentrations of the conventional anesthetics are sufficient to achieve good anesthesia at the treated site.

The following specific examples will further serve to illustrate the compositions of this invention.

EXAMPLE 1

The procedure described below together with the results obtained according to the procedure will further illustrate the antimicrobial compositions of this invention and their unusual degree of effectiveness. The procedure entails admixing (1) 3 ml citrated human blood, (2) 5 ml peptone water, (3) 1 ml cell suspension (bacteria, yeast or fungi), and (4) 1 ml of a test solution, which test solution comprises 40% ethanol and may include either or both of an antimicrobial agent and a potentiator. The first three components are admixed and preincubated at room temperature for ten minutes before the addition of the test solution.

After the ten minute preincubation period, the test solution comprising 40% ethanol, alone or together with the antimicrobial agent alone, the potentiator alone, or the combination of the two, is added. At intervals of 1, 10 and 30 minutes after this final addition one ml of the treated mixtures is removed and transferred to a dilution tube that contains 9 ml of a neutralizing composition comprising peptone water and an antimicrobial neutralizer. The neutralizer is required to inactivate the unadsorbed antimicrobial agent that otherwise may give rise to false positive results. After neutralization, serial dilutions are made with peptone water, and each dilution is plated out in a petri dish, and then covered with 15 ml of trypticase soy or Mycophil agar media. The plates are incubated at appropriate temperature for two to three days, then the colonies are counted at each dilution. The number of surviving organisms are determined by multiplying the number of colonies that are counted at the lowest dilution with the power of that dilution.

A series of the following four solutions was prepared in accordance with the foregoing procedure:

|  |  |  |
|---|---|---|
| I | ethanol | 40% |
|  | water | 60% |
| II | ethanol | 40% |
|  | water | 60% |
|  | + |  |
|  | antimicrobial agent; |  |
| III | ethanol | 40% |
|  | water | 57% |
|  | + |  |
|  | potentiator; and |  |
| IV | ethanol | 40% |
|  | water | 57% |
|  | + |  |
|  | antimicrobial agent |  |
|  | + |  |
|  | potentiator. |  |

TABLE I

BACTERICIDAL (KILLING) EFFICACY

| | | | Number of Cells Survived | | |
|---|---|---|---|---|---|
| | | | Contact Times: | | |
| Organism | Solution | | 1 minute | 10 minutes | 30 minutes |
| S. aureus | I | | $3.2 \times 10^9$ | $3.1 \times 10^9$ | $3.2 \times 10^9$ |
| | II | (1) | $2.3 \times 10^7$ | $1.9 \times 10^7$ | $1.0 \times 10^7$ |
| | III | (2) | $7.0 \times 10^5$ | $6.0 \times 10^3$ | 460 |
| | IV | (3) | 0 | 0 | 0 |
| S. aureus | I | | $3.2 \times 10^9$ | $3.1 \times 10^9$ | $3.2 \times 10^9$ |
| | II | (4) | $2.3 \times 10^7$ | $1.9 \times 10^7$ | $1.0 \times 10^7$ |
| | III | (5) | $8.9 \times 10^7$ | $8.6 \times 10^7$ | $1.6 \times 10^7$ |
| | IV | (6) | $4.0 \times 10^6$ | $7.0 \times 10^3$ | 90 |
| C. albicans | I | | $9.1 \times 10^8$ | $9.0 \times 10^8$ | $8.2 \times 10^8$ |
| | II | (4) | $9.0 \times 10^8$ | $8.2 \times 10^8$ | $7.1 \times 10^8$ |
| | III | (7) | $3.0 \times 10^8$ | $8.8 \times 10^8$ | $3.0 \times 10^3$ |
| | IV | (8) | $1.6 \times 10^6$ | $4.0 \times 10^3$ | 30 |
| C. albicans | I | | $2.5 \times 10^9$ | $3.0 \times 10^9$ | $3.5 \times 10^9$ |
| | II | (9) | $3.8 \times 10^6$ | $2.5 \times 10^6$ | $2.4 \times 10^6$ |
| | III | (10) | $9 \times 10^6$ | $7.5 \times 10^6$ | $4 \times 10^6$ |
| | IV | (11) | $9 \times 10^5$ | 0 | 0 |
| C. albicans | I | | $2.5 \times 10^8$ | $2.2 \times 10^8$ | $2.9 \times 10^8$ |

TABLE I-continued
BACTERICIDAL (KILLING) EFFICACY

| Organism | Solution | | 1 minute | 10 minutes | 30 minutes |
|---|---|---|---|---|---|
| | II | (12) | $3.4 \times 10^7$ | $3.5 \times 10^7$ | $3.5 \times 10^7$ |
| | III | (13) | $8.0 \times 10^7$ | $1.2 \times 10^7$ | $5 \times 10^5$ |
| | IV | (14) | $6.0 \times 10^5$ | 20 | 0 |
| C. albicans | I | | $1.3 \times 10^9$ | $1.0 \times 10^9$ | $1.0 \times 10^9$ |
| | II | (15) | $9 \times 10^8$ | $8.0 \times 10^8$ | $7 \times 10^8$ |
| | III | (16) | $1.7 \times 10^6$ | $2 \times 10^3$ | $2 \times 10^3$ |
| | IV | (17) | $5 \times 10^4$ | 0 | 0 |
| P. aeruginosa | I | | $9.2 \times 10^8$ | $9.0 \times 10^8$ | $9.6 \times 10^8$ |
| | II | (18) | $7.4 \times 10^8$ | $7.0 \times 10^8$ | $6.8 \times 10^8$ |
| | III | (19) | $1.1 \times 10^6$ | $7.8 \times 10^4$ | $4.8 \times 10^4$ |
| | IV | (20) | $1.9 \times 10^4$ | 1 | 0 |
| P. aeruginosa | I | | $9.2 \times 10^8$ | $9.0 \times 10^8$ | $9.6 \times 10^8$ |
| | II | (18) | $7.4 \times 10^8$ | $7.0 \times 10^8$ | $6.8 \times 10^8$ |
| | III | (21) | $8.5 \times 10^6$ | $7.6 \times 10^6$ | $5.1 \times 10^6$ |
| | IV | (22) | $8.0 \times 10^3$ | $3.0 \times 10^3$ | $9.0 \times 10^2$ |
| C. albicans | I | | $1.1 \times 10^9$ | $1.2 \times 10^9$ | $1.2 \times 10^9$ |
| | II | (18) | $2.8 \times 10^7$ | $2.6 \times 10^7$ | $2.7 \times 10^7$ |
| | III | (23) | $2.6 \times 10^6$ | $3.0 \times 10^5$ | $1.6 \times 10^4$ |
| | IV | (24) | $2.8 \times 10^3$ | 20 | 0 |
| S. aureus | I | | $2.4 \times 10^9$ | $2.0 \times 10^9$ | $2.1 \times 10^9$ |
| | II | (18) | $1.4 \times 10^9$ | $1.2 \times 10^9$ | $9.2 \times 10^8$ |
| | III | (21) | $1.3 \times 10^8$ | $3.0 \times 10^5$ | $1.0 \times 10^4$ |
| | IV | (22) | $2.9 \times 10^7$ | $2.0 \times 10^3$ | 80 |
| C. albicans | II* | (25) | $12 \times 10^7$ | $12 \times 10^7$ | $12 \times 10^7$ |
| | III* | (26) | $17 \times 10^7$ | $40 \times 10^5$ | $10 \times 10^5$ |
| | IV* | (27) | $11 \times 10^6$ | $10 \times 10^3$ | $10 \times 10^3$ |
| S. aureus | II* | (25) | $40 \times 10^8$ | $40 \times 10^8$ | $40 \times 10^8$ |
| | III* | (26) | $50 \times 10^7$ | $10 \times 10^5$ | $30 \times 10^3$ |
| | IV* | (27) | $20 \times 10^6$ | 0 | 0 |
| S. aureus | II | (28) | $13 \times 10^7$ | $13 \times 10^7$ | $14 \times 10^7$ |
| | III | (29) | $84 \times 10^6$ | $17 \times 10^4$ | $60 \times 10^3$ |
| | IV | (30) | $13 \times 10^6$ | $10 \times 10^2$ | 500 |

(1) Domiphen bromide (0.0125%)
(2) Hexanol (0.6%)
(3) Domiphen bromide (0.0125%) + hexanol (0.6%)
(4) Domiphen bromide (0.0250%)
(5) 2-Heptanol (0.5%)
(6) Domiphen bromide (0.0250%) + 2-Heptanol (0.50%)
(7) 2,3-Dimethyl-2-hexanol (0.50%)
(8) Domiphen bromide (0.0250%) + 2,3-Dimethyl-2-hexanol (0.50%)
(9) Hibitane (0.050%)
(10) 2-Cyclohexylphenol (0.1%)
(11) Hibitane (0.05%) plus 2-cyclohexylphenol (0.1%)
(12) Griseofulvin (0.05%)
(13) 2,3-Dimethyl-2-hexanol (0.5%)
(14) Griseofulvin (0.05%) + 2,3-Dimethyl-2-hexanol (0.5%)
(15) Zn-omadine (0.1%)
(16) 2-Cyclohexylethanol (0.6%)
(17) Zn-omadine (0.1%) + 2-Cyclohexylethanol (0.6%)
(18) Miconazole-NO$_3$ (0.05%)
(19) 2-Cyclohexylethanol (0.4%)
(20) Miconazole-NO$_3$ (0.05%) + 2-Cyclohexylethanol (0.4%)
(21) 2,3-Dimethyl-2-hexanol (0.75%)
(22) Miconazole-NO$_3$ (0.05%) + 2,3-Dimethyl-2-hexanol (0.75%)
(23) 1-Cyclohexylethanol (0.75%)
(24) Miconazole-NO$_3$ (0.05%) + 1-Cyclohexylethanol (0.75%)
(25) Rifampicin (0.0125%)
(26) 2-Cyclohexylethanol (0.6%)
(27) Rifampicin (0.0125%) + 2-cyclohexylethanol (0.6%)
(28) Ag-sulfadiazine (0.050%)
(29) 2-Cyclohexylethanol (0.5%)
(30) Ag-sulfadiazine (0.050%) + 2-cyclohexylethanol (0.5%)
*Bacteriostatic activity can be observed up to 0.00125%

Thus, it can be seen that when the antimicrobial compositions of this invention are employed, the killing efficacy of the antimicrobial agent in the presence of blood is greatly enhanced.

In a similar manner, additional antimicrobial compositions of this invention have been tested and a summary of the test results appears in Table II.

TABLE II
BACTERICIDAL (KILLING) EFFICACY

| Organism | Solution | | 1 minute | 10 minutes | 30 minutes |
|---|---|---|---|---|---|
| C. albicans | | Tetracycline (0.05%) | $4.3 \times 10^7$ | $3.9 \times 10^7$ | $3.6 \times 10^7$ |
| | A* | + 1-(p-chlorophenyl)-2-methyl-2-propanol (0.5%) | $1.8 \times 10^6$ | 1950 | 0 |
| C. albicans | | Tetracycline (0.05%) | $4.3 \times 10^7$ | $3.9 \times 10^7$ | $3.6 \times 10^7$ |
| | A | + 1-cyclohexyl-1-ethanol (0.50%) | $1.3 \times 10^7$ | $2.9 \times 10^4$ | 110 |
| C. albicans | | Neomycin SO$_4$ (0.05%) | $6.4 \times 10^7$ | $4.2 \times 10^7$ | $2.6 \times 10^7$ |
| | A | + 1-cyclohexyl-1-ethanol (0.75%) | $8.8 \times 10^5$ | $1.9 \times 10^3$ | 100 |
| C. albicans | | Erythromycin (0.025%) | $7.2 \times 10^8$ | $7.1 \times 10^8$ | $9.2 + 10^7$ |
| | A | + 2,3-Dimethyl-2-hexanol (0.75%) | $1.5 \times 10^6$ | $1.3 \times 10^4$ | 0 |
| S. aureus | | Erythromycin (0.025%) | $4.9 \times 10^7$ | $4.6 \times 10^7$ | $4.3 \times 10^7$ |
| | A | + 2,3-Dimethyl-2-hexanol (0.75) | $1.2 \times 10^6$ | $2.0 \times 10^4$ | 500 |
| S. aureus | | Tetracycline (0.05%) | $4.2 \times 10^8$ | $4.1 \times 10^8$ | $3.8 \times 10^7$ |
| | A | + 1-(p-chlorophenyl)-2-methyl-2-propanol (0.5%) | $1.7 \times 10^7$ | $1.0 \times 10^4$ | 100 |
| S. aureus | | Tetracycline (0.05%) | $4.2 \times 10^8$ | $4.1 \times 10^8$ | $3.8 \times 10^7$ |
| | A | + 2-Cyclohexyl-1-propanol (0.40%) | $2.1 \times 10^7$ | $2.0 \times 10^5$ | 1000 |
| S. aureus | | Benzalkonium chloride (0.05%) | $9.0 \times 10^5$ | $1.0 \times 10^5$ | $2.9 \times 10^3$ |
| | A | + 1-Cyclohexylethanol (0.40%) | $1.0 \times 10^3$ | 10 | 0 |
| S. aureus | | Benzalkenium chloride (0.05%) | $9.0 \times 10^5$ | $1.0 \times 10^5$ | $2.9 \times 10^3$ |
| | A | +1-Cyclohexyl-1-propanol (0.60%) | $6.0 \times 10^3$ | 700 | 0 |
| S. aureus | | 3,4,4'-Chlorocarbanilide (0.05%) | $6.1 \times 10^7$ | $5.2 \times 10^7$ | $3.0 \times 10^7$ |
| | A | + 2-Cyclohexyl-1-propanol (0.40%) | $4.2 \times 10^7$ | $1.0 \times 10^5$ | 3200 |
| S. aureus | | Temasept IV** (0.05%) | $4.2 \times 10^8$ | $4.0 \times 10^8$ | $1.2 \times 10^8$ |
| | A | + 2-Cyclohexyl ethanol (0.4%) | $3.9 \times 10^7$ | $1.0 \times 10^4$ | 20 |
| S. aureus | | 5-iodo-2-deoxyuridine (0.2%) | $30 \times 10^7$ | $30 \times 10^7$ | $30 \times 10^7$ |
| S. aureus | A | + 2-cyclohexylethanol (0.6%) | $10 \times 10^3$ | $10 \times 10^2$ | 100 |
| S. aureus | | Cycloserine (0.0125%) | $60 \times 10^7$ | $60 \times 10^7$ | $60 \times 10^7$ |
| S. aureus | A | + 2-cyclohexylethanol (0.6%) | $74 \times 10^5$ | $12 \times 10^3$ | 500 |
| C. acnes | | Erythromycin (0.0125%)*** | $22 \times 10^5$ | $21 \times 10^5$ | $18 \times 10^5$ |
| C. acnes | A | + 2-cyclohexylethanol (0.3%) | $70 \times 10^3$ | 0 | 0 |
| C. acnes | | Dequalinium chloride (0.00125%) | $26 \times 10^5$ | $14 \times 10^2$ | 30 |
| C. acnes | A | + 2-cyclohexylethanol (0.3%) | $81 \times 10^3$ | 0 | 0 |
| C. acnes | | Rifampicin (0.0125%)*** | $17 \times 10^6$ | $17 \times 10^6$ | $13 \times 10^6$ |
| C. acnes | A | + 2-cyclohexylethanol (0.6%)*** | $80 \times 10^3$ | 0 | 0 |
| C. acnes | | Hibitane (0.0125%) | $45 \times 10^6$ | $51 \times 10^5$ | 0 |

TABLE II-continued

BACTERICIDAL (KILLING) EFFICACY

| Organism | Solution | Number of Cells Survived Contact Times: | | |
|---|---|---|---|---|
| | | 1 minute | 10 minutes | 30 minutes |
| C. acnes | A + 2-cyclohexylethanol (0.3%) | 0 | 0 | 0 |
| C. acnes | Griseofulvin (0.0125%) | $94 \times 10^5$ | $99 \times 10^5$ | $92 \times 10^3$ |
| C. acnes | A + 2-cyclohexylethanol (0.3%) | $50 \times 10^4$ | $11 \times 10^3$ | 90 |

*A represents the immediately preceding antimicrobial in the indicated concentration e.g., tetracycline (0.05%); neomycin $SO_4$ (0.05%) etc.
**3,4',5-tribromosalicylanilide
***Bacteriostatic activity can be observed up to 0.00125%

EXAMPLE 2

| Anti-plaque mouthrinse composition | |
|---|---|
| Ethanol | 20% |
| Glycerine USP | 10% |
| Flavor | 0.2% |
| Domiphen Bromide | from 0.05 to 0.10% |
| 2-Cyclohexylethanol | from 0.1 to 3.0% |
| Amaranth solution | 0.04% |
| Distilled water q.s. to 100% | |

To use this mouthwash solution, the mouth is rinsed with 15 to 20 ml for 30 to 60 seconds twice daily. In vitro models show a reduction of 85 to 95% in dental plaque formation as compared to controls under identical experimental conditions.

EXAMPLE 3

| Surgical Scrub | |
|---|---|
| Potentiator, 1-(p-chlorophenol)-2-methyl-2 propanol | 3.0 to 6.0% |
| Antimicrobial, Irgasan DP 300 (2,4,4'-Trichloro-2'-hydroxy-diphenyl-ether) | 0.05 to 0.25% |
| Surfactant, Emcol E607 | 2.0% |
| Glycerine USP | 5.0% |
| P.E.G. 6000 distearate | 1.5% |
| Distilled water q.s. to | 100% |

To use this surgical scrub, the hands are rubbed together with 10 to 15 ml of the above solution for one to three minutes in the same manner as currently used surgical scrub solutions.

EXAMPLE 4

| Hard Surface Disinfectant | |
|---|---|
| Potentiator, 2,3-Dimethyl-2-hexanol | 3.0 to 10% |
| Antimicrobial, Dequalinium Cl | 0.05 to 3.0% |
| Iso-propanol | 40.0% |
| Propylene glycol | 5.0% |
| Distilled water q.s. to | 100.00% |

In using this disinfectant, the solution is spread onto the surface with a soft cloth, or by spraying in the form of an aerosol spray, resulting in sterilization of the surface within one to five minutes.

EXAMPLE 5

| Wound Irrigating Solution | |
|---|---|
| Antimicrobial, Domiphen bromide | 0.125% |
| Potentiator, 1-Cyclohexyl-1-propanol | 3.0% |

| Wound Irrigating Solution (continued) | |
|---|---|
| Ethanol or isopropanol | 40.0% |
| Distilled water | 56.87% |

In tests and operative techniques carried out according to the procedure set forth in F. Goldschmidt, Reproducible Topical Staphylococcal Infection in Rats, Applied Microbiology, 23, No. 1, p. 130 (1972), established infections with abscess formation were demonstrated in 91.4% of the infected control animals with recoverable Staphylococcus areus in amounts of $10^5$ cells or more per gram of excised body wall.

In the experimental group composition of this Example, infection was prevented, abscess did not develop, and Staphylococcus aureus could be recovered only from 28.6% of the animals in amounts of $10^5$ or more cells per gram of excised body wall. Using 3.0% 1-cyclohexyl-1-propanol alone, abscess formation occurred in 100% of the animals, with recoverable Staphylococcus aureus in amounts of $10^6$ cells or more per gram of excised body wall. With domiphen bromide alone, abscess formation occurred in, and Staphylococcus aureus could be recovered from, 82.3% of the animals in amounts of $10^5$ or more cells per gram of excised body wall.

In summary, approximately five out of seven animals responded to the combination therapy, whereas neither agent alone was sufficient to prevent the infection.

EXAMPLE 6

To illustrate the enhanced penetration of the topical compositions of the invention, the following formulation was employed to prepare compositions which were then tested in a standardized skin blanching test wherein the degree of blanching corresponds to the degree of penetration. The results are shown in Table III.

| | FORMULATION | |
|---|---|---|
| Ethanol | 50.00 | % w/w |
| Propylene glycol | 10.00 | |
| Cetyl alcohol | 0.50 | |
| dl-Epinephrine | 0.10 | |
| Dithiothreitol | 0.001 | |
| Water | 29.40 | |
| Penetrant potentiator | 10.00 | |
| | 100.00 | |

Note - In formula (1) of Table III below the above formulation was varied by substituting ethanol for the penetrant potentiator, so that formula (1) contained a total of 60% w/w ethanol.

TABLE III

PENETRATION OF EPINEPHRINE THROUGH THE INTACT HUMAN SKIN

| Combinations | Time Elapsed After Application | | | | | |
|---|---|---|---|---|---|---|
| | 10 min | 20 min | 30 min | 40 min | 50 min | 60 min |
| Epinephrine (E) 0.05% | 0 | 0-1 | 0 | 0 | 0 | 0 |

TABLE III-continued
PENETRATION OF EPINEPHRINE THROUGH THE INTACT HUMAN SKIN

| Combinations | Time Elapsed After Application | | | | | |
|---|---|---|---|---|---|---|
| | 10 min | 20 min | 30 min | 40 min | 50 min | 60 min |
| E + pentanol | 0 | 0 | 0 | | | |
| E + hexanol | 0 | 1-2 | 0-1 | | | |
| E + heptanol | 0-1 | 0-1 | 0 | | | |
| E +2-heptanol | 0 | 1 | 0 | | | |
| E + 2,3-dimethyl-2-hexanol | 0 | 0-1 | 0-1 | | | |
| E + dimethyl sulfoxide | 0 | 0 | 0 | | | |
| E + 1-cyclohexylethanol | 1 | 1-2 | 1-2 | —* | 1-2 | |
| E + 1,1-dimethylcyclohexyl methanol | 0-1 | 0-1 | 1-2 | — | 1-3 | |
| E + (4-isopropylcyclohexyl)-dimethyl carbinol | 0-1 | 1 | 2-3 | — | 3 | 3 |
| E + 1-cyclohexyl-1-propanol | 0-1 | 2 | 2-3 | — | 3 | 3 |
| E + 2-cyclohexylethanol | 1 | 1 | 1 | — | — | 1-3 |
| E + 1-cyclohexyl-1-butanol | 0-1 | 0-1 | 0 | — | — | 1-2 |
| E + 2-cyclohexyl-2-methyl propanol | 1-2 | 2-3 | — | 3 | | |
| E + 2-cyclohexyl-1,1-dimethyl ethanol | 0 | 1-2 | — | 2-3 | | |
| E + 1-phenyl-2-methyl-2-propanol | 0 | 1 | 1-2 | 1-3 | | |
| E + benzyl-t-butanol | 1-2 | 3 | 3 | 1-3 | | |

Scoring grade:
0) no visible blanching
1) slight visible blanching
2) medium blanching
3) very strong blanching
(All the alcohol potentiators were used in 10% concentration)
*A - means not tested at this time interval. Also some compositions were only tested for 30, 40 or 50 minutes.

EXAMPLE 7

| Topical Anesthetic Solution Formulation | |
|---|---|
| Ethanol | 10 -0 80.0% w/w |
| Penetrant Accelerator | 1 - 12.0% |
| Anesthetic Agent | 1 - 10.0% |
| Water q.s. to pH 8.0 | 100.0% |

EXAMPLE 8

| Topical Anesthetic Gel Formulation | |
|---|---|
| Ethanol | 50.0% w/w |
| Penetrant Accelerator | 12.0% |
| Anesthetic Agent | 4.0% |
| Water | 31.0% |
| Klucel HF | 3.0% |

EXAMPLE 9

| Topical Anesthetic Gel Formulation | |
|---|---|
| Ethanol | 21.0% w/w |
| Penetrant Accelerator | 12.0% |
| Anesthetic Agent | 4.0% |
| Dibutylphthalate | 35.0% |
| Isopropylmyristate | 23.0% |
| Cabosil | 5.0% |

EXAMPLE 10

| Topical Anesthetic Solution Formulation | |
|---|---|
| Ethanol | 50.0% w/w |
| Propylene Glycol | 10.0% |
| Anesthetic Agent | 4.0% |
| Penetrant Accelerator | 12.0% |
| Water | 24.0% |

EXAMPLE 11

| Topical Anesthetic Solution Formulation | |
|---|---|
| Ethanol | 50.0% |
| Propylene Glycol | 10.0% |
| Cetyl Alcohol | 0.5% |
| Anesthetic Agent | 4.0% |
| Penetrant Accelerator | 10.0% |
| Water | 25.5% |

When the formulations of Examples 7-11, prepared using lidocaine HCl as the anesthetic agent and 2-cyclohexyl-1,1-dimethyl ethanol as the pentrant accelerator, were applied topically to intact human skin with a "BAND-AID" ® brand ashesive bandage, surface to deep anesthesia was obtained within 15 to 60 minutes. The onset time of anesthesia was rapid (15 to 30 minutes) and anesthesia lasted for several hours (3 to 6 hours). The results of similar studies are summarized in Tables IV and V.

EXAMPLE 12

Similar animal studies with guinea pigs, the preparation being applied onto the intact skin, showed that the combination of the anesthetic with the penetrant accelerator elicits quick and deep anesthesia at the treated site (<5 min.), the anesthesia lasting up to several hours. These results are summarized in Table VI.

"In vitro" percutaneous absorption studies with intact guinea pig skin showed that the combination of lidocaine with a penetrant accelerator results in 20 to 30 fold more lidocaine penetration through the intact skin than without the accelerator.

TABLE IV

| | ANESTHETIC RESPONSE | | | |
|---|---|---|---|---|
| | TIME IN MINUTES | | | |
| FORMULA | 30-35 | 60-70 | 110-120 | 250-300 |
| A* | 0/4 (0%) | 0/4 (0%) | 0/4 (0%) | 0/4 (0%) |
| B** | 9/13 (69.2%) | 13/14 (92.8%) | 13/13 (100%) | 6/10 (60%) |

A* = 5% Lidocaine HCl in 50% aqueous ethanol
B** = 4% Lidocaine in 50% aqueous ethanol with 10% propylene glycol plus 12% 2-cyclohexyl-1,1-dimethyl ethanol.

TABLE V

| | | ANESTHETIC RESPONSE | | | |
|---|---|---|---|---|---|
| | Degree of | TIME IN MINUTES | | | |
| Formula | Anesthesia | 30-35 | 60-70 | 110-120 | 250-300 |
| C* | 0 | 4/13 | 1/14 | 0/13 | 4/16 |

TABLE V-continued

| | ANESTHETIC RESPONSE | | | |
|---|---|---|---|---|
| | Degree of | TIME IN MINUTES | | | |
| Formula | Anesthesia | 30-35 | 60-70 | 110-120 | 250-300 |
| 1 | | (30.8%) 9/13 | (72%) 3/14 | (0%) 4/13 | (40%) 5/10 |
| 2 | | (69.2%) | (21.4%) 3/14 | (30.8%) 3/13 | (50%) 1/10 |
| 3 | | | (21.4%) 7/14 (50%) | (23.1%) 6/13 (46.1%) | (10%) |

DEGREE OF ANESTHESIA:
0 - No anesthesia
1 - Slight anesthesia
2 - Moderate anesthesia
3 - Profound anesthesia
C* = 4% Lidocaine in 50% aqueous ethanol with 10% propylene glycol plus 12% α,α-dimethyl-2-cyclohexylethanol

TABLE VI

| LOCAL ANESTHESIA FOLLOWING TWO APPLICATIONS TO INTACT SKIN - TESTED FOLLOWING 2ND APPLICATION ONLY | | | |
|---|---|---|---|
| FORMULA | NO. AFFECTED NO. TESTED | ONSET (MIN.) | DURATION (MIN.) |
| D | 0/6 | — | — |
| E | 6/6 | <5 | 15-30 |
| F | 0/6 | — | — |
| G | 6/6 | <5 | >120 |

FORMULA D = 45% Ethanol
FORMULA E = 12% 2-Cyclohexylethanol in 45% Ethanol
FORMULA F = 4% Lidocaine in water, pH 4.0
FORMULA G = 4% Lidocaine plus 12% 2-Cyclohexylethanol in 45% Ethanol, pH 3.0

Thus, it can be seen that when the anesthetic compositions of this invention are employed, the anesthetic activity of the conventional anesthetic agents is greatly enhanced even through the intact skin.

As will be apparent to those skilled in the art, many changes and modifications may be made which do not depart from the scope or spirit of the invention.

What is claimed is:

1. A topical anesthetic composition comprising an effective amount of a topical anesthetic agent and an amount of a penetrant accelerator effective to enhance the skin penetration of said anesthetic agent, said penetrant accelerator being selected from the group consisting of the cyclohexyl substituted alkanols of the structure

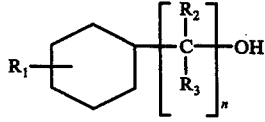

wherein $R_1$ is $C_1$ to $C_4$ alkyl, halogen or hydrogen; $R_2$ and $R_3$ are independently selected from hydrogen, $C_1$ to $C_3$ alkyl, and cyclopropyl; and $n$ is 1 to 4, provided that only one of said $R_2$ and $R_3$ may be propyl or cyclopropyl.

2. The topical anesthetic composition of claim 1 wherein said penetrant accelerator is at least one primary, secondary or tertiary cyclohexylalkanol or alkylcyclohexyl alkanol selected from the group consisting of cyclohexylmethanol, 1-cyclohexylethanol, 2-cyclohexylethanol, 1-cyclohexyl-1-propanol, (cyclohexyl)-dimethyl-carbinol, (4-isopropylcyclohexyl)-dimethylcarbinol, 3-cyclohexyl-1-propanol, 2-cyclohexyl-1-propanol, 1-cyclohexyl-2-propanol, 2-cyclohexyl-1,1-dimethylethanol, 2-cyclohexyl-2-methylpropanol, 2-cyclohexyl-1-methylpropanol, 2-cyclohexyl-1, 2-dimethylpropanol, 2-cyclohexyl-1, 1-dimethylpropanol, 3-cyclohexyl-2-methylpropanol, 3-cyclohexyl-1-methylpropanol, 3-cyclohexylbutanol, 3-cyclohexyl-2-methylbutanol and 3-cyclohexyl-1, 2-dimethylbutanol.

3. The topical anesthetic composition of claim 1 wherein said anesthetic agent is selected from the group consisting of lidocaine, benzocaine, tetracaine, carbocaine and rodocaine, and said penetrant accelerator is at least one primary, secondary or tertiary cyclohexylalkanol or alkylcyclohexyl alkanol selected from the group consisting of cyclohexylmethanol, 1-cyclohexylethanol, 2-cyclohexylethanol, 1-cyclohexyl-1-propanol, (cyclohexyl)-dimethyl-carbinol, (4-isopropylcyclohexyl)-dimethylcaarbinol, 3-cyclohexyl-1-propanol, 2-cyclohexyl-1-propanol, 1-cyclohexyl-2-propanol, 2-cyclohexyl-1,1-dimethylethanol, 2-cyclohexyl-2-methylpropanol, 2-cyclohexyl-1-methyl-propanol, 2-cyclohexyl-1, 2-dimethylpropanol, 2-cyclohexyl-1, 1-dimethylpropanol, 3-cyclohexyl-2-methylpropanol, 3-cyclohexyl-1-methylpropanol, 3-cyclohexylbutanol, 3-cyclohexyl-2-methylbutanol and 3-cyclohexyl-1, 2-dimethylbutanol.

4. The topical anesthetic composition of claim 1 wherein the anesthetic agent comprises Lidocaine HCl and the penetrant accelerator comprises 2-cyclohexyl-1, 1-dimethylethanol.

5. The anesthetic composition of claim 1 wherein the anesthetic agent comprises Lidocaine and the penetrant accelerator comprises 2-cyclohexylethanol.

6. The composition of claim 4 which further comprises about 50% ethanol, about 10% propylene glycol, and distilled water.

7. The composition of claim 5 which further comprises about 45% ethanol.

8. The anesthetic composition of claim 1 which further comprises a pharmaceutically acceptable carrier.

9. The anesthetic composition of claim 1 which contains up to about 12% of the anesthetic agent, up to about 15% of the penetrant accelerator, and a pharmaceutically acceptable carrier selected from the group consisting of water, the lower alkanols and propylene glycol.

10. The composition of claim 9 which contains from about 1% to about 10% anesthetic agent and from about 1% to about 12% penetrant accelerator.

11. The composition of claim 9 in which said carrier is aqueous ethanol.

12. The anesthetic composition of claim 9 in which said carrier is aqueous ethanol plus propylene glycol.

13. The topical composition of claim 1 wherein the anesthetic agent is selected from the group consisting of lidocaine, benzocaine, tetracaine, carbocaine and rodocaine.

14. The topical composition of claim 1 in which the penetrant accelerator is selected from the group consisting of cyclohexylmethanol, 1-cyclohexylethanol, 2-cyclohexylethanol, 1-cyclohexyl-1-propanol, (cyclohexyl)-dimethyl carbinol, (4-isopropylcyclohexyl)-dimethylcarbinol, 3-cyclohexyl-1-propanol, 2-cyclohexyl-1-propanol, 1-cyclohexyl-2-propanol, 2-cyclohexyl-1, 1-dimethylethanol, 2-cyclohexyl-2-methylpropanol, 2-cyclohexyl-1-methylpropanol, 2-cyclohexyl-1,2-dimethylpropanol, 2-cyclohexyl-1, 1-dimethylpropanol, 3-cyclohexyl-2-methylpropanol, 3-cyclohexyl-1-methylpropanol, 3-cyclohexylbutanol, 3-cyclohexyl-2-methylbutanol and 3-cyclohexyl-1,2-dimethylbutanol.

15. The topical composition of claim 1 in which the amount of penetrant accelerator is from about 1 to about 12% by weight of the composition.

16. The topical composition of claim 1 which includes from about 0.5 to about 12% by weight of said anesthetic agent.

17. The topical composition of claim 16 wherein the amount of anesthetic agent is from about 1% to about 10% by weight.

18. The topical composition of claim 3 which further includes a pharmaceutically acceptable carrier.

19. The topical composition of claim 18 in which the carrier is selected from the group consisting of water, the lower alkanols and propylene glycol.

20. The topical composition of claim 19 in which said carrier comprises water.

21. The topical composition of claim 1 in the form of an ointment, cream, lotion, aerosol preparation, suspension or solution.

22. A method of inducing anesthesia topically comprising applying to the skin of an animal a topical composition of claim 1.

23. In the topical inducement of anesthesia by applying to the skin of an animal a topical anesthetic agent, the improvement comprising potentiating the activity or penetration of the anesthetic agent by applying the same in conjunction with a potentiator which is a primary, secondary or tertiary cyclohexylalkanol or alkylcyclohexyl alkanol selected from the group consisting of cyclohexylmethanol, 1-cyclohexylethanol, 2-cyclohexylethanol, 1-cyclohexyl-1-propanol, (cyclohexyl)-dimethylcarbinol, (4,isoproyl-cyclohexyl)-dimethylcarbinol, 3-cyclohexyl-1-propanol, 2-cyclohexyl-1-propanol, 1-cyclohexyl-2-propanol, 2-cyclohexyl-1, 1-dimethylethanol, 2-cyclohexyl-2-methylpropanol, 2-cyclohexyl-1-methylpropanol, 2-cyclohexyl-1, 2-dimethylpropanol, 2-cyclohexyl-1, 1-dimethylpropanol, 3-cyclohexyl-2-methylpropanol, 3-cyclohexyl-1-methylpropanol, 3-cyclohexylbutanol, 3-cyclohexyl-2-methylbutanol and 3-cyclohexyl-1, 2-dimethylbutanol.

24. The method of claim 23 wherein the anesthetic agent comprises Lidocaine HCl and the penetrant accelerator comprises 2-cyclohexyl-1, 1-dimethylethanol.

25. The method of claim 23 wherein the anesthetic agent comprises Lidocaine and the penetrant accelerator comprises 2-cyclohexylethanol.

* * * * *

UNITED STATES PATENT AND TRADEMARK OFFICE
CERTIFICATE OF CORRECTION

PATENT NO. : 4,091,090

DATED : May 23, 1978

INVENTOR(S) : Tibor Sipos

It is certified that error appears in the above—identified patent and that said Letters Patent is hereby corrected as shown below:

Col. 10, line 63, Table I, C. albicans III(7), under column entitled "30 minutes" - "$3.0 \times 10^3$" should be --$5.0 \times 10^5$--

Col. 10, line 67, Table I, C. albicans III(10), under column entitled "30 minutes" - "$4 \times 10^6$" should be --$4 \times 10^5$--

Col. 11, line 19, Table 1, C. albicans IV(24), under column entitled "1 minute" - "$2.8 \times 10^3$" should be --$2.8 \times 10^5$--

Col. 12, lines 1-6 - the entire heading preceding the footnotes should be deleted Col. 12, line 22 - should be rewritten to read "Miconazole-$NO_3$ (0.05%)+2,3-Dimethyl-2-hexanol(0.75%)"

Cols. 13 & 14, Table II, under column entitled "30 minutes" - "$92 \times 10^3$" should be --$92 \times 10^5$--

UNITED STATES PATENT AND TRADEMARK OFFICE
CERTIFICATE OF CORRECTION

PATENT NO. : 4,091,090

DATED : May 23, 1978

INVENTOR(S) : Tibor Sipos

It is certified that error appears in the above—identified patent and that said Letters Patent is hereby corrected as shown below:

Col. 17, line 29 - "pH 3.0" should be ---pH 8.0---

Col. 18, line 14 - "dimethylcaarbinol" should be ---dimethylcarbinol---

Signed and Sealed this

Twenty-first Day of September 1982

[SEAL]

Attest:

Attesting Officer

GERALD J. MOSSINGHOFF

Commissioner of Patents and Trademarks